(12) United States Patent
Jordan et al.

(10) Patent No.: US 10,470,776 B2
(45) Date of Patent: Nov. 12, 2019

(54) TISSUE CLOSURE

(71) Applicant: BOSTON SCIENTIFIC SCIMED, INC., Maple Grove, MN (US)

(72) Inventors: Gary Jordan, Litchfield, NH (US); Barry Weitzner, Acton, MA (US); Michael Zupkofska, Rockland, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 402 days.

(21) Appl. No.: 15/246,293

(22) Filed: Aug. 24, 2016

(65) Prior Publication Data

US 2016/0361065 A1 Dec. 15, 2016

Related U.S. Application Data

(63) Continuation of application No. 13/241,677, filed on Sep. 23, 2011, now Pat. No. 9,451,967.

(60) Provisional application No. 61/408,849, filed on Nov. 1, 2010.

(51) Int. Cl.
| | | |
|---|---|---|
| *A61B 17/128* | (2006.01) | |
| *A61B 17/04* | (2006.01) | |
| *A61B 17/122* | (2006.01) | |
| *A61B 17/22* | (2006.01) | |
| *A61B 17/30* | (2006.01) | |
| *A61M 1/00* | (2006.01) | |
| *A61B 17/00* | (2006.01) | |

(52) U.S. Cl.
CPC ........ *A61B 17/128* (2013.01); *A61B 17/0469* (2013.01); *A61B 17/122* (2013.01); *A61B 17/1227* (2013.01); *A61B 17/1285* (2013.01); *A61B 17/22031* (2013.01); *A61B 17/30* (2013.01); *A61M 1/008* (2013.01); *A61B 17/0482* (2013.01); *A61B 2017/00867* (2013.01); *A61B 2017/306* (2013.01)

(58) Field of Classification Search
None
See application file for complete search history.

(56) References Cited

U.S. PATENT DOCUMENTS

| | | | | |
|---|---|---|---|---|
| 6,015,417 A | * | 1/2000 | Reynolds, Jr. ....... | A61B 17/064 606/151 |
| 6,582,451 B1 | * | 6/2003 | Marucci ................ | A61B 17/29 606/207 |
| 2007/0118163 A1 | * | 5/2007 | Boudreaux .......... | A61B 17/064 606/157 |

* cited by examiner

*Primary Examiner* — Shaun L David
(74) *Attorney, Agent, or Firm* — Fay Kaplun & Marcin, LLP

(57) ABSTRACT

A device for fastening tissue includes (a) a shaft extending longitudinally from a distal end insertable into a body to a proximal end attached to a controller which remains outside of the body, the shaft including a lumen extending therethrough and an opening extending through a wall of a distal portion thereof to open the lumen to an exterior of the shaft; (b) a first roller housed within the lumen adjacent to a first longitudinal edge of the opening such that a rotation of the first roller grasps and draws tissue from the body into the lumen in combination; and (c) a fastening element housed within the lumen adjacent to the opening and movable from a tissue receiving configuration to a tissue gripping configuration.

12 Claims, 5 Drawing Sheets

TISSUE CLOSURE

PRIORITY CLAIM

The present application is a Continuation of U.S. patent application Ser. No. 13/241,677 filed on Sep. 23, 2011, now U.S. Pat. No. 9,451,967; which claims priority to U.S. Provisional Patent Application Ser. No. 61/408,849 filed on Nov. 1, 2010. The entire disclosures of these patents/applications are expressly incorporated herein by reference.

BACKGROUND

The closure of perforations in tissue caused by procedures such as large intra-luminal resections, is an important capability for advanced minimally invasive procedures. Hemostatic clips are widely used by surgeons to close small gaps and prevent bleeding. However, large perforations often cannot be adequately treated with these hemostatic clips.

SUMMARY OF THE INVENTION

The present invention relates to a device for fastening tissue, comprising a shaft extending longitudinally from a distal end insertable into a living body to a proximal end attached to a controller which remains outside of the body, the shaft including at least one lumen extending therethrough and an elongated opening extending through a wall of a distal portion thereof to open the lumen to an exterior of the shaft and a first roller housed within the lumen adjacent to a first longitudinal edge of the opening such that a rotation of the first roller grasps and draws tissue into the lumen via the opening in combination with a fastening element housed within the lumen adjacent to the opening and movable from a tissue receiving configuration to a tissue fastening configuration.

DETAILED DESCRIPTION

Figure 1:
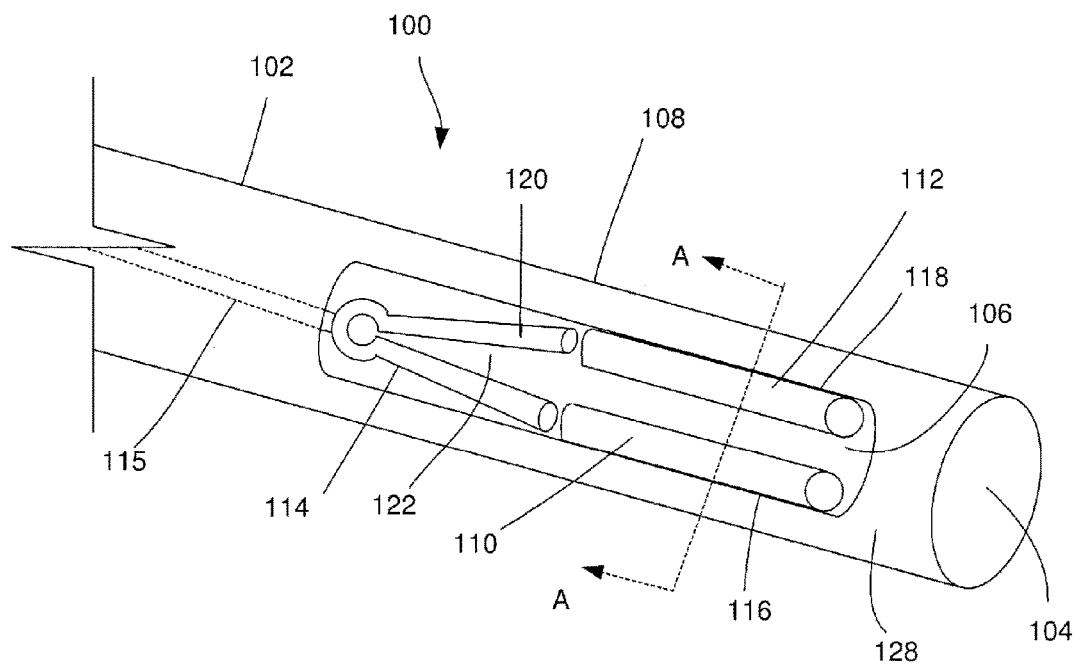
FIG. 1 shows a perspective view of a distal portion of a device according to a first exemplary embodiment of the present invention.

The present invention may be further understood with reference to the following description and the appended drawings, wherein like elements are referred to with the same reference numerals. The present invention relates to devices for tissue approximation and, in particular, relates to devices for fastening tissue. Exemplary embodiments of the present invention describe a device including rollers that draw edges of tissue together such that the approximated edges of the perforation may be clipped and/or sutured together. Although exemplary embodiments of the present invention specifically describe devices for clipping and fastening perforations, it will be understood by those of skill in the art that the present invention may be similarly used to clip ducts, blood vessels and airways, etc.

Figure 2:
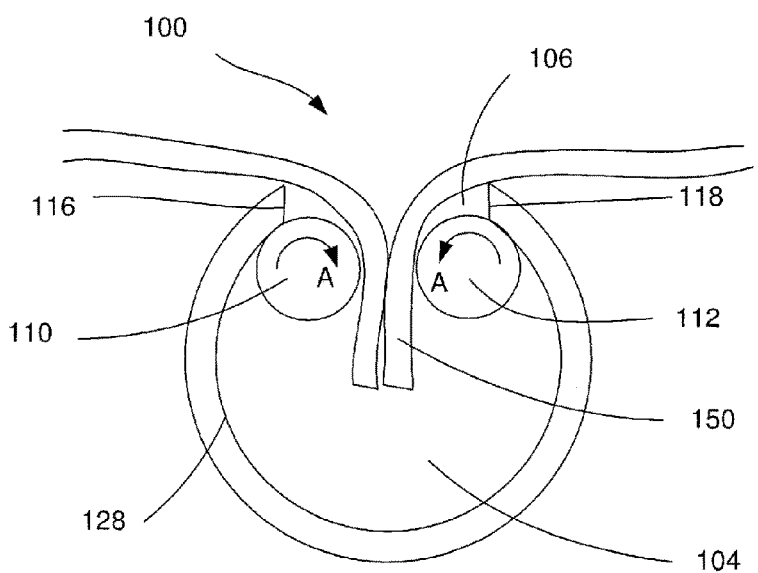
FIG. 2 shows a cross-sectional view of the distal portion of the device of FIG. 1, along line A-A.

As shown in FIGS. 1-2, a device 100 according to a first exemplary embodiment of the present invention comprises a shaft 102 including a lumen 104 extending longitudinally therethrough. The shaft 102 includes an opening 106 extending laterally through a wall 128 of a distal portion 108 through which edges of a perforation are drawn into the lumen 104. The opening 106 may be configured as, for example, a window or a slot extending through the wall 28. The device 100 further comprises first and second rollers 110, 112 housed within the lumen 104 for drawing tissue 150 therein through the opening 106 and a clip 114 clipping the edges of the tissue 150 together once the tissue 150 has been drawn into the lumen 104 in contact with one another. As would be understood by those skilled in the art, a proximal end of the shaft 102 may be coupled to a handle, control mechanism and/or actuating mechanism (not shown) for actuating a rolling mechanism of the pair of rollers 110, 112 and for moving the clip 114 from a first configuration to a second configuration. The distal portion 108 is inserted into a living body while the proximal end of the shaft 102 remains outside of the body. The proximal end of the shaft 102 may be coupled to a vacuum source for applying a suctioning force through the opening 106 to draw edges of tissue adjacent thereto between the rollers 110, 112. However, those skilled in the art will understand that other mechanisms such as, for example, graspers, may be employed to draw tissue into the opening 106.

The opening 106 may be elongated, extending longitudinally along the distal portion 108 a distance greater than a width thereof (i.e., an extent of the opening 106 around a circumference of the shaft 102). The first and second rollers 110, 112 are housed within the lumen 104 with the first roller 110 positioned adjacent a first longitudinal edge 116 of the opening 106 while the second roller 112 is positioned adjacent to a second longitudinal edge 118 of the opening 106 opposite the first roller 110. The first and second rollers 110, 112 are spaced apart from one another by a distance selected to permit the tissue 150 to be drawn at least partially into a space therebetween through the application of negative pressure via the lumen 104. The first and second rollers 110, 112 may also include a plurality of openings extending through a wall thereof such that a negative pressure may also be applied through the rollers 110, 112 to both pull tissue into the opening 106 and to create a grip on the tissue. In another embodiment, at least one of the rollers 110, 112 may extend slightly through the opening 106 so that the roller 110, 112 functions as a tissue grasper, drawing the tissue 150 through the opening 106. The rollers 110, 112 are attached to an actuating mechanism (not shown) (e.g., at the proximal end of the shaft 102) via drive shafts that rotate the rollers 110, 112 in the direction of arrows A with portions of the rollers 110, 112 adjacent to the opening 106 rotating toward the center of the lumen 104 to draw edges of tissue positioned between the rollers 110, 112 further into the lumen 104 between the rollers 110, 112, as shown in FIG. 2. In a further embodiment, the rollers 110, 112 may be moved relative to one another to adjust the space therebetween. For example, an initial space between the rollers 110, 112 may be selected to permit tissue to be drawn therebetween. Once tissue has been drawn between the rollers 110, 112, as desired, the rollers 110, 112 may be moved toward one another to reduce the amount of space therebetween, holding the tissue 150 therebetween for fastening.

The outer surface of one or both of the rollers 110, 112 may be treated to increase friction against the tissue 150. For example, the outer surface may be treated to increase friction against the tissue 150. For example, at least one of the rollers 110, 112 may be treated to include a coating with a non-slip material or a coating that roughens a surface thereof. Alternatively, the outer surface may include tissue gripping features such as, for example, barbs, teeth, divots and spikes, which facilitate a gripping and/or pulling of the tissue 150. Although two rollers 110, 112 are specifically described herein, it will be understood by those of skill in the art that the device 100 may alternatively include a single roller positioned adjacent an edge of the opening 106 to draw tissue therein as the roller rotates.

The fastener 114 is housed within the lumen 104 and is movable between a first configuration in which the fastener 114 is positioned proximally of the rollers 110, 112 and a second configuration in which the fastener 114 is moved distally relative to the shaft 102 to fastener the tissue 150 approximated by the rollers 110, 112. The fastener 114 may be connected to the actuator at the proximal end of the shaft 102 via for example, a pusher 115 which pushes the fastener 114 from the first configuration to the second configuration. The exemplary fastener 114 includes a plurality of arms 120 configured to grip the approximated edges of tissue therebetween. However, those skilled in the art will understand that fasteners of any number of configurations may be employed without departing from the scope of the invention. A length of the arms 120 may be selected to be at least as long as a length of a tissue attachment site such as, for example, a perforation, so that edges of the tissue may be entirely gripped therebetween allowing the tissue attachment site to be entirely sealed with a single fastener 114.

In one exemplary embodiment, the fastener 114 is formed of an elastic, spring-like material with the arms 120 biased toward a clipping configuration in which the arms 120 are separated by a distance corresponding to a thickness of the edges of the tissue 150 to be gripped thereby. That is, the arms may be biased toward a position in which, when a target thickness of tissue is received therebetween, the arms 120 exert a desired clipping force to the tissue while the elasticity of the arms 120 permits the arms to spread apart slightly as they are deployed over the tissue 150 allowing the tissue to be slid into the fastener 114. Thus, the size of a space 122 between the arms 120 when the fastener 114 is in an unstressed state is sized to facilitate both receipt of the tissue 150 and to achieve a desired gripping force after the tissue has been properly positioned within the fastener 114.

Figure 3:
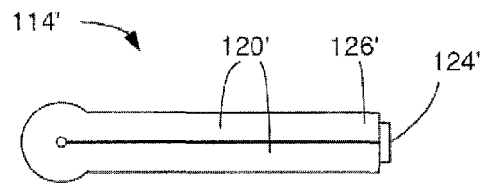
FIG. 3 shows a side view of a clip according to an alternate embodiment of the present invention.

In another embodiment, as shown in FIG. 3, a fastener 114' may include a plurality of arms 120' biased toward an open configuration to receive the approximated edges of tissue 150 therebetween. The fastener 114' may include a locking mechanism 124' at a distal end 126' thereof. The arms 120' may be moved toward one another and the locking mechanism 124' may be locked to lock the arms 120' relative to one another, fixing the tissue therebetween after the tissue has been positioned as desired between the arms 120'. The locking mechanism 124' may include, for example, a first coupling element at a distal end of a first arm 120' and a second coupling element at a distal end of a second arm 120', which are configured to couple to one another. In some cases, where tissue extends beyond a distal end of the fastener 114', the first coupling element may be capable of penetrating tissue to connect to the second connecting element. Once tissue has been positioned between the arms 120' as desired, the arms 120' may be drawn together via, for example, a capture sleeve deployed to move over the arms 120', an external grasping mechanism, a clamping mechanism or a spring mechanism.

An exemplary tissue fastening technique according to the present invention, includes insertion of the device 100 into a living body (e.g., via a naturally occurring bodily orifice) such until the distal portion 108 is adjacent a tissue perforation to be treated. A vacuum source may then be activated to apply a vacuum force through the lumen 104 drawing edges of the perforation through the opening 106 in proximity to the rollers 110, 112. The rollers 110, 112 may then be actuated so that the rollers 110, 112 rotate inward relative to one another to draw the edges of the tissue 150 therebetween into the lumen 104 gripping the tissue 150 between the rollers 110, 112. Once the edges 150 are gripped between the rollers 110, 112, as desired, the approximated edges 150 are fastened together via the fastener 114, which is moved to the second configuration with the approximated edges 150 slidably received between the arms 120 thereof. The arms 120 fasten the edges together, providing closure of the perforation. Where the fastener 114' is used, the lock 124' may be locked such that the arms 120' are fixed relative to one another and the tissue 150 is permanently gripped therebetween. Upon closure of the perforation, the shaft 102 may be removed from the body leaving the fastener 114 in position over the fastened tissue. The fastener 114 may remain in the body either temporarily or permanently. The fastener 114 may be resorbable or eventually fall off after healing of the perforation. Alternatively, the fastener 114 may be surgically removed after healing.

Figure 4:
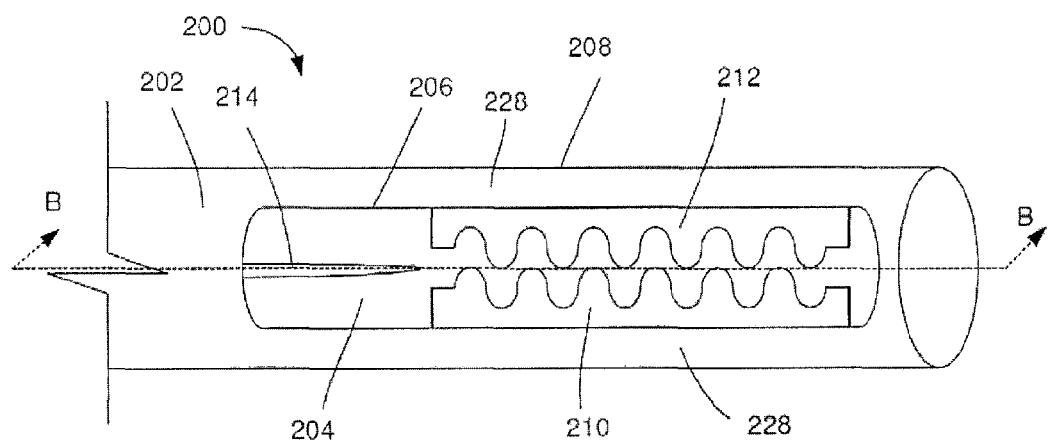
FIG. 4 shows a perspective view of a distal portion of a device according to a second exemplary embodiment of the present invention.
Figure 5:
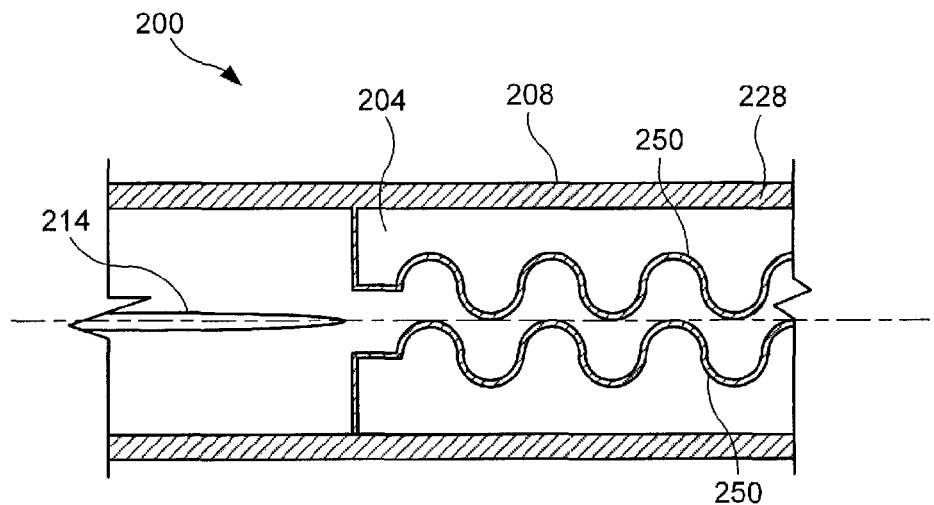
FIG. 5 shows a cross-sectional view of the distal portion of the device of FIG. 4, along line B-B.

As shown in FIGS. 4-5, a device 200 according to another exemplary is be substantially similar to the device 100, comprising a shaft 202 including a lumen 204 extending therethrough. The shaft 202 further includes a longitudinally shaped opening 206 extending laterally through a wall 228 of a distal portion 208 thereof with rollers 210, 212 positioned adjacent to the opening 206 similarly to the rollers 110, 112 of the device 100 described above. The device 200, however, includes a needle 214 rather than a fastener. In addition, the rollers 210, 212 have outer surfaces 230, 232, respectively, that are complementary such that tissue received therebetween is shaped into folds. A raised portion along the outer surface 230 of the first roller may correspond to a grooved portion along the outer surface 232 of the second roller 212 such that the tissue drawn therebetween includes a fold along a length thereof. For example, the outer surfaces 230, 232 may correspondingly extend in a sinusoidal, wave-like pattern along a length thereof such that a peak of the first roller 210 corresponds to a trough of the second roller 212. Thus, as the rollers 210, 212 are rotated inward relative to one another, edges of the tissue 250 are drawn therebetween in a corresponding wave-like pattern such that the tissue 250 includes folds along a length thereof, as shown in FIG. 4.

A needle 214 may be substantially straight including a filament such that advancement of the needle 214 distally relative to the shaft 202 passes the needle 214 through the folds of the approximated tissue 250, fastening the approximated edges together. The filament may be, for example, a wire, a suture thread, etc. The needle 214 may be moved distally via, for example, a push mechanism, which advances the needle through the tissue 250. The needle 214 may extend distally past a distal end of the tissue 250 such that the filament extends through the folds of the tissue 250, securing the edges of the tissue 250 together. The needle 214 may be captured at distal end of the device 200. Beads, stops or other locking elements may be affixed to the proximal and/or distal ends of the filament to hold the filament within the tissue and/or permit a desired tension to be applied on the filament. Alternatively, the filament may be cut and fastened via, for example, a surgical knot. It will be understood by those of skill in the art that the device may additionally include a cutting mechanism configured to cut the filament after the edges of the tissue have been secured. Alternatively, a cutting tool may be passed down to the surgical site. The surgical knot applied to the filament may be, for example, a pusher knot in which filament ends are retracted out of the body, knotted, and then advanced back to the tissue. The filament may be formed of any known biocompatible and/or resorbable material so that the suture may remain in place or dissolve over time. In an alternative embodiment, the needle 214 itself may be used as the fastener so that a filament is not required. The needle 214 is passed through the folds of the tissue 250 and is held therein via, for example, any of the locking elements described above. Similarly, the needle 214 may remain in place, dissolve or degrade over time. The needle 214 may be formed of a material that is stiff upon deployment to pass through the tissue 250, but which softens over time.

Figure 6:
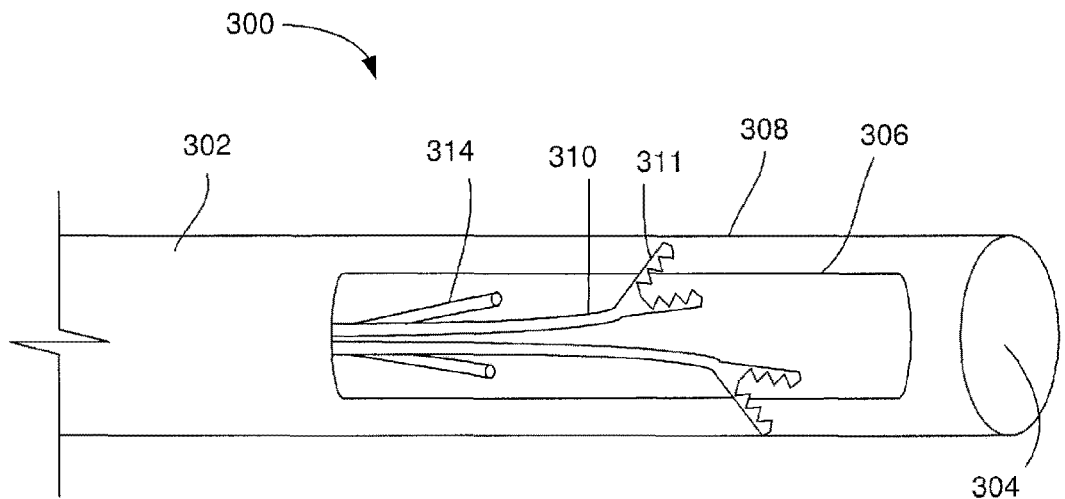
FIG. 6 shows a perspective view of a distal portion of a device according to a third exemplary embodiment of the present invention.

As shown in FIG. 6 a device 300 according to another embodiment may be substantially similar to the device 100, as described above, comprising a shaft 302 including a lumen 304 extending therethrough. Similarly to the device 100, a distal portion 308 of the shaft 302 includes a opening 306 through which tissue may be drawn into the lumen 304. The device 300, however, does not include rollers for drawings tissue therein. Rather, the device 300 includes one or more tissue graspers 310, which are controllable via a control mechanism attached to a proximal end of the shaft 302. The tissue graspers 310 may include jaws 311 movable relative to one another to grasp tissue therebetween as would be understood by those skilled in the art. In another embodiment, the tissue graspers 310 may include hooks or other tissue grasping elements. Once the distal portion 308 has been positioned adjacent a penetration in a target portion tissue, the tissue graspers 310 are moved out of the opening 306 to grasp the edges of the tissue, drawing the edges together into the lumen 304. As described above in regard to device 100, a vacuum force may be applied through the lumen 304 to assist in drawing the edges of the tissue toward the opening 306 facilitating grasping of the edges by the tissue grasper 310. In another embodiment, the tissue grasper 310 may be a vacuum grasper separate from the vacuum in the shaft 302. The vacuum grasper may include, for example, a vacuum line and a flexible cup at a distal end thereof for grasping tissue via a vacuum force exerted through the vacuum line.

Once the target tissue has been drawn into the lumen 304 via the opening 306, a fastener 314 is moved distally within shaft 302 to fasten the approximated edges together. The fastener 314 may be substantially similar to any of the fastener configurations described above in regard to the device 100. Those skilled in the art will understand that any of the fasteners described in regard to this invention may alternatively be housed in a portion of the shaft distal to the opening and moved proximally over the tissue drawn into the lumen to fasten the target tissue.

Figure 7:
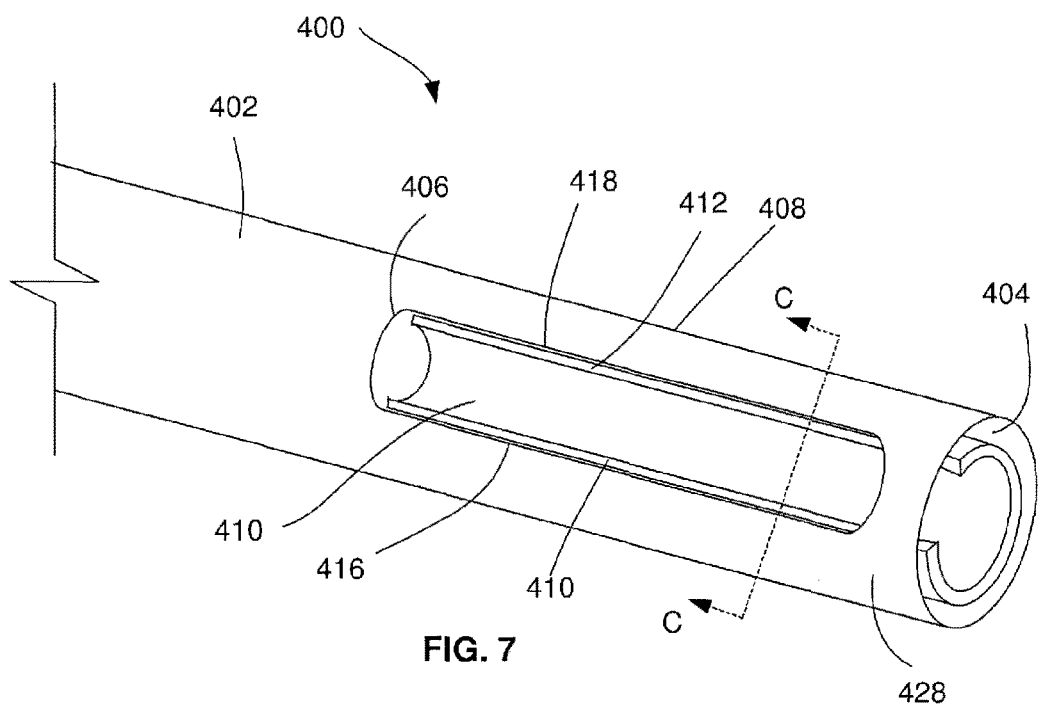
FIG. 7 shows a perspective view of a distal portion of a device according to a fourth exemplary embodiment of the present invention.
Figure 8:
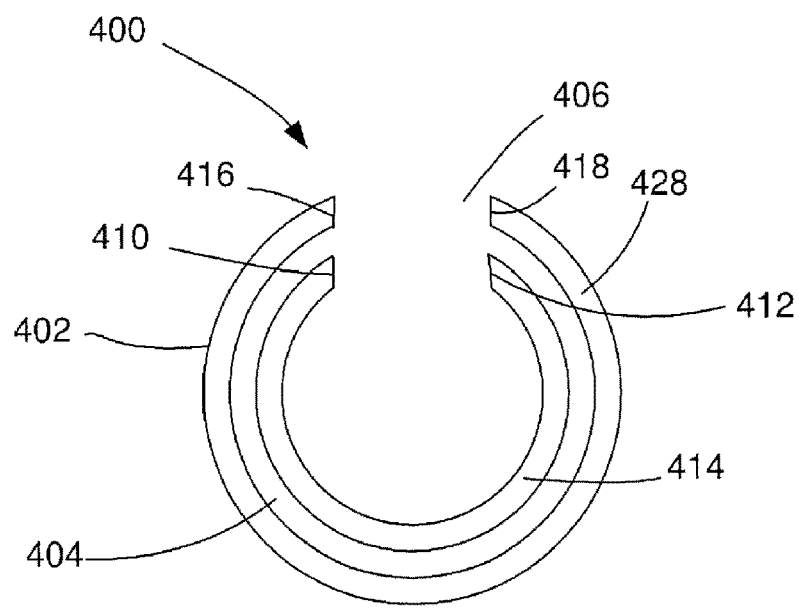
FIG. 8 shows a cross-sectional view of the distal portion of the device of FIG. 7 in a first configuration, along line C-C.
Figure 9:
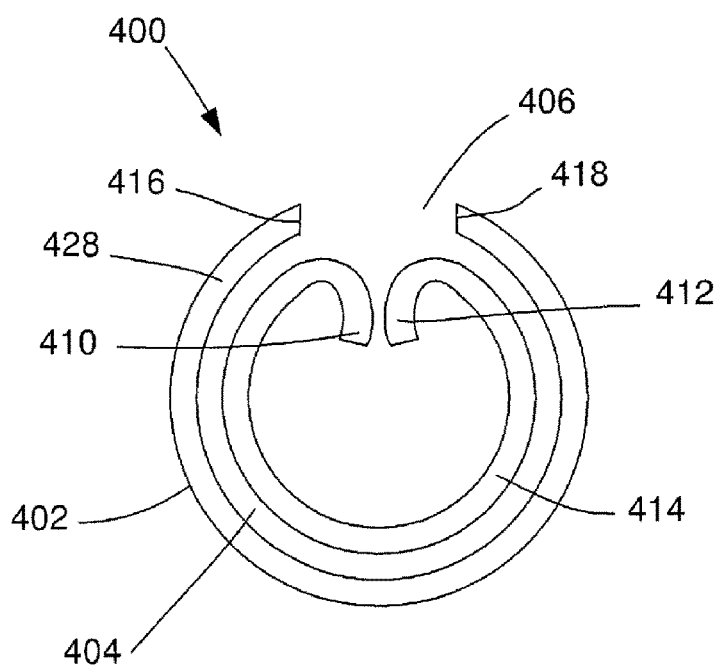
FIG. 9 shows a cross-sectional view of the distal portion of the device of FIG. 7, in a second configuration.

As shown in FIGS. 7-9, a device 400 according to another embodiment of the present invention may be substantially similar to the device 100, as described above, comprising a shaft 402 including a lumen 404 extending longitudinally therethrough and a opening 406 extending transversely through a wall 428 of a distal portion 408 thereof. Rather than rollers and a fastener including arms, however, the device 400 comprises a fastener 414 housed within the distal portion 408 of the shaft 402. The fastener 414 is curved along a longitudinal axis thereof such that target tissue may be received between longitudinal edges 410, 412 of the fastener 414. The longitudinal edges 410, 412 are movable between a first tissue receiving configuration, as shown in FIG. 8, and a second tissue gripping configuration, as shown in FIG. 9. Similarly to the rollers 110, 112 in the device 100, the first longitudinal edge 410 of the fastener 414 may be positioned adjacent a first longitudinal edge 416 of the opening 406 and the second longitudinal edge 412 may be positioned adjacent a second longitudinal edge 418 of the opening 406. Thus, as tissue is drawn through the opening 406 into the lumen 404, the tissue is received between the longitudinal edges 410, 412 of the fastener 414.

Figure 10:
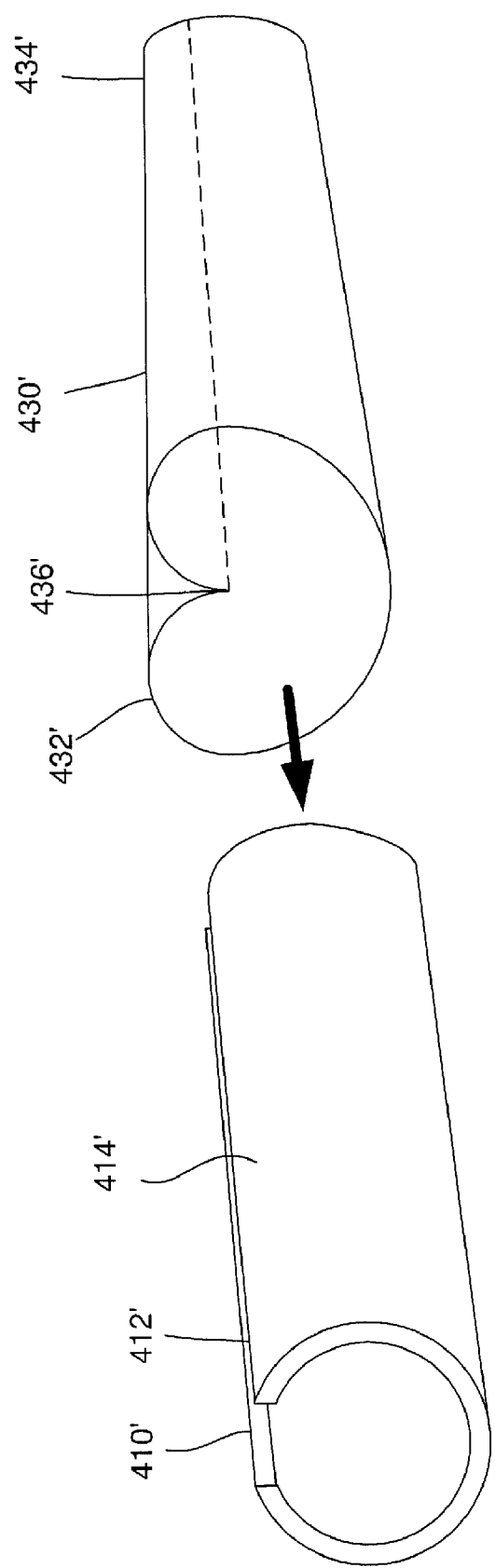
FIG. 10 shows a perspective view of a fastener of the device of FIG. 7, according to an alternate embodiment of the present invention.

The fastener 414 may be a spring clip formed of a shape memory material which, when activated, moves from the first configuration to the second configuration. The fastener 414 may be activated by, for example, providing mechanical or electrical stimulation. Activation of the fastener 414 moves the fastener 414 from the first configuration in which the longitudinal edges 410, 412 thereof are spaced apart in a tissue receiving configuration, to the second configuration in which the longitudinal edges 410, 412 are moved toward one another to fasten tissue therebetween. In another embodiment, the fastener 414 may be formed of an elastic or superelastic material that is held open while tissue is drawn between the longitudinal edges 410, 412 thereof and snapped shut when the holding force is removed. The tissue may be drawn into the opening 406 using any known method such as a suctioning force, tissue graspers, etc. In a further embodiment, the longitudinal edges 410, 412 may be shaped to roll inward with respect to one another, as shown in FIG. 9 so that tissue drawn toward the opening 406 via, for example, a suctioning force, is gripped and drawn between the inwardly rolling edges 410, 412 as the fastener 414 is activated and moved to the second configuration. In another embodiment, as shown in FIG. 10, the fastener 414' may be plastically deformed such that longitudinal edges 410', 412' roll inward via a tubular die 430' that is moved over the fastener 414'. The tubular die 430' tapers from a first end 432' to a second end 434' and includes an edge 436' that is curled inward along a length thereof. The edge 436' may correspond to a desired curvature of the longitudinal edges 410', 412' in the second configuration such that as the tubular die 430' is moved over the fastener 414', the longitudinal edges 410', 412' are moved from the first configuration to the second configuration. It will be understood by those of skill in the art, however, that the fastener 414 may be any type of locking fastener formed of any material such as an elastic, superelastic and/or plastic material, that permits the fastener 414 to be moved from the first configuration to the second configuration. To enhance the gripping capabilities of the edges 410, 412 of the fastener 414, the edges 410, 412 may include teeth, serrations or other elements to facilitate gripping of the tissue. The edges 410, 412 may also be treated with a coating to facilitate gripping by, for example, roughening a surface thereof.

It will be understood by those skilled in the art that various modifications and variations can be made in the structure and the methodology of the present intention, without departing from the spirit or scope of the invention. Thus, it is intended that the present invention cover the medications and variations of this invention provided that they come within the scope of the appended claims and their equivalents.

What is claimed is:

1. A device for fastening tissue, comprising:
a shaft extending longitudinally from a distal end insertable into a body to a proximal end attached to a controller which, when the shaft is inserted into the body, remains outside of the body, the shaft including a lumen extending longitudinally therethrough and an opening extending laterally through a wall of a distal portion of the shaft so that the lumen is open to an exterior of the shaft via the opening; and
a substantially tubular clip housed within the lumen adjacent to the opening and movable from a tissue receiving configuration to a tissue gripping configuration, the tubular clip extending along a longitudinal axis thereof and including a longitudinal slot extending therealong to define a first tissue fastening edge and a second fastening edge, the first fastening edge being adjacent to a first longitudinal edge of the opening and the second fastening edge being adjacent to a second longitudinal edge of the opening, the first and second fastening edges being spaced apart in the tissue receiving configuration to receive target tissue therebetween and being moved toward one another in the tissue gripping configuration to grip target tissue therebetween, wherein the first and second fastening edges roll inward toward one another as the clip moves from the tissue receiving configuration to the tissue gripping configuration gripping target tissue received therebetween so that the rolling of the first and second fastening edges relative to one another pulls the target tissue farther into the lumen as the clip is moved to the tissue gripping configuration.

2. The device of claim 1, wherein the proximal end of the shaft is configured to be connected to a vacuum source for applying a vacuum force through the lumen of the shaft to draw the target tissue through the opening.

3. The device of claim 1, wherein the clip is a spring clip formed of a shape memory material which, when activated, moves from the tissue receiving configuration to the tissue gripping configuration.

4. The device of claim 1, wherein the clip is activated to move from the tissue receiving configuration to the tissue gripping configuration via one of a mechanical and an electrical stimulation.

5. The device of claim 1, wherein the clip is formed of an elastic material that is held in the tissue receiving configuration via a removable holding element in the tissue receiving configuration so that, when the holding element is removed, the clip reverts to the tissue gripping configuration.

6. The device of claim 1, wherein the first and second fastening edges include tissue gripping structures.

7. The device of claim 6, wherein the tissue gripping structures include one of teeth and serrations.

8. The device of claim 1, wherein the first and second fastening edges are treated with a coating for facilitating gripping of the target tissue.

9. The device of claim 1, further comprising a tubular die movable relative to the longitudinal axis of the clip and including an edge that is curled inward along a length thereof such that, when the die is moved over the clip, the curled edge forces the first and second fastening edges to roll inward toward the tissue gripping configuration.

10. The device of claim 9, wherein the tubular die tapers from a distal end to a proximal end thereof.

11. The device of claim 1, further comprising tissue graspers configured to grasp and draw tissue through the opening.

12. The device of claim 11, wherein the tissue graspers include one of jaws and hooks.

* * * * *